United States Patent
Sugihara et al.

(10) Patent No.: US 7,154,988 B2
(45) Date of Patent: *Dec. 26, 2006

(54) X-RAY COMPUTED TOMOGRAPHIC IMAGING APPARATUS

(75) Inventors: Naoki Sugihara, Nasu-gun (JP); Nobukatsu Soejima, Nasu-gun (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 11/197,484

(22) Filed: Aug. 5, 2005

(65) Prior Publication Data

US 2005/0265514 A1    Dec. 1, 2005

Related U.S. Application Data

(63) Continuation of application No. 10/197,827, filed on Jul. 19, 2002, now Pat. No. 6,990,170.

(30) Foreign Application Priority Data

Aug. 9, 2001 (JP) ............................ 2001-241755
Nov. 27, 2001 (JP) ............................ 2001-361346

(51) Int. Cl.
*A61B 6/03* (2006.01)

(52) U.S. Cl. ........................................... 378/15; 378/4

(58) Field of Classification Search ................... 378/4, 378/15, 147, 150, 901, 16
See application file for complete search history.

(56) References Cited

U.S. PATENT DOCUMENTS

| 5,270,923 A | 12/1993 | King et al. |
| 5,454,019 A | 9/1995 | Migita et al. |
| 5,485,493 A * | 1/1996 | Heuscher et al. ............. 378/15 |
| 5,627,868 A | 5/1997 | Nobuta et al. |
| 5,734,691 A | 3/1998 | Hu et al. |
| 5,825,842 A | 10/1998 | Taguchi |
| 6,373,916 B1 | 4/2002 | Inoue et al. |

FOREIGN PATENT DOCUMENTS

| JP | 8-275937 | 10/1996 |
| JP | 11-9582 | 1/1999 |
| JP | 2000-225114 | 8/2000 |
| JP | 2001-145621 | 5/2001 |
| JP | 2001-212128 | 8/2001 |
| JP | 2003-102720 | 4/2003 |

* cited by examiner

*Primary Examiner*—Courtney Thomas
*Assistant Examiner*—Chih-Cheng Glen Kao
(74) *Attorney, Agent, or Firm*—Oblon, Spivak, McClelland, Maier & Neustadt, P.C.

(57) ABSTRACT

An X-ray computed tomography apparatus includes a cone beam X-ray tube, an X-ray detector, a rotating mechanism for supporting the X-ray tube and X-ray detector, a moving mechanism for moving the object in the slice direction, a control unit for controlling the rotating mechanism and moving mechanism to execute helical scan operation and move relative to the object, an input device for setting a substantially cylindrical reconstruction area, and an image reconstructing unit for reconstructing image data within the set reconstruction area based on the output of the detector. The apparatus also includes a movement distance determining unit for determining the movement distance of the X-ray tube and X-ray detector relative to the object on the basis of the radius of the set reconstruction area as well as its height.

7 Claims, 17 Drawing Sheets

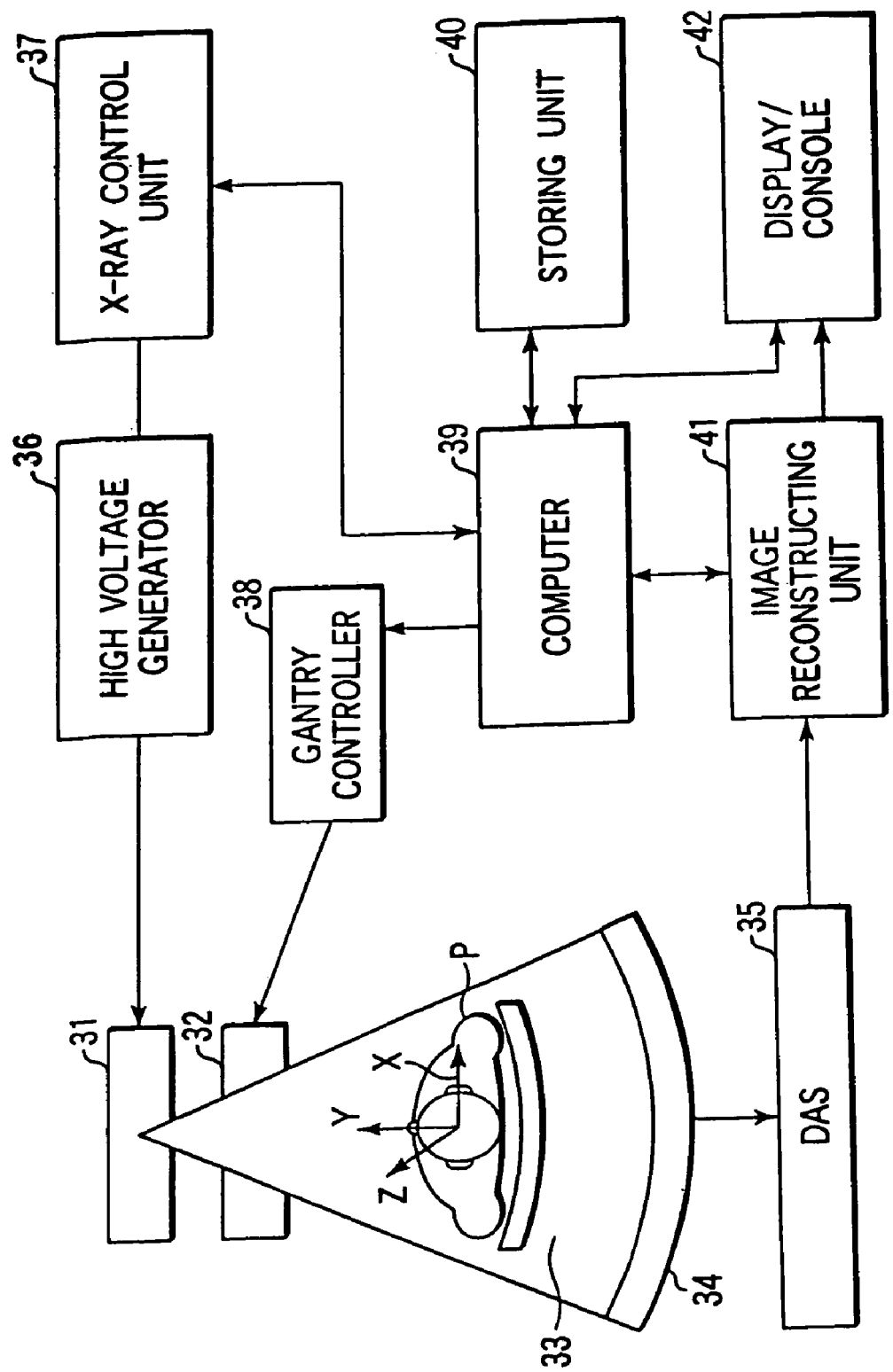
F I G. 15

X-RAY COMPUTED TOMOGRAPHIC IMAGING APPARATUS

CROSS-REFERENCE TO RELATED APPLICATIONS

This application is a continuation of and claims the benefit of priority from U.S. patent application Ser. No. 10/197,827, filed on Jul. 19, 2002 now U.S. Pat. No. 6,990,170, which claims the benefit of priority from Japanese Patent Application No. 2001-241755, filed on Aug. 9, 2001, and from Japanese Patent Application No. 2001-361346, filed on Nov. 27, 2001, the entire contents of all of which are incorporated herein by reference.

BACKGROUND OF THE INVENTION

1. Field of the Invention

The present invention relates to a multi-slice or cone-beam X-ray computed tomography apparatus.

2. Description of the Related Art

A cone-beam CT apparatus has a larger number of detector arrays and a wider X-ray divergence angle in the slice direction than a multi-slice CT apparatus. Typically, the number of detector arrays mounted in a multi-slice CT apparatus is, for example, 4, 8, or 16, whereas that in a cone-beam CT apparatus reaches as many as 256 or 512.

Such a cone-beam CT apparatus can perform "helical scan" like a single-slice CT apparatus or multi-slice CT apparatus. Helical scan is a technique of obtaining data while an X-ray tube and X-ray detector relatively move in the slice direction (substantially parallel to the body axis direction of an object to be examined) while rotating around the object. In helical scan, the X-ray tube moves along a helical path around the object. Helical scan allows acquisition of data in a wide range within a short period of time.

As indicated by the hatching in FIG. 1, in helical scan, an examiner sets an FOV (Field Of View). Image data is reconstructed within the field of view. A field of view is synonymous with a reconstruction area.

In helical scan, an X-ray tube 111 generates X-rays in a section where it moves, together with a detector 112, by a distance X relative to an object to be examined. This distance X is set to be equivalent to a length H of a reconstruction area FOV. This results in unnecessary areas (shaded portions) irradiated with X-rays in spite of the fact that no image data is reconstructed outside the reconstruction area FOV. As shown in FIG. 2, these unnecessary areas are produced regardless of radiuss S and SS.

The following problem arises in a cone-beam CT apparatus. In the case of a single-slice CT apparatus, as shown in FIG. 3, the operator sets the width (radius or radius; radius in this case) of the circular reconstruction area FOV, which actually has a thin cylindrical shape having a thickness, and a slice thickness, in addition to a tube voltage, tube current, scan time, and the like. The opening degree of a X-ray stop (collimator) 102 for limiting the divergence angle (called the cone angle) of X-rays from an X-ray tube 101 in the slice direction is adjusted such that the thickness of an X-ray beam coincides with the set slice thickness on a rotational axis (Z-axis). At this time, the peripheral portions of the reconstruction area FOV which are indicated by the hatching in FIG. 3 are irradiated with no X-rays. That is, the data of these portions are omitted from the corresponding areas (hatched portions) when each view is taken into account. Although the data is acquired in a view at an opposite direction, this data omission affects the image quality of the peripheral portions of an MPR image. In practice, however, in single-slice CT, the volume ratio of the data omission portion to the reconstruction area FOV is very much limited, and hence no significant problem arises.

This problem, however, becomes evident in cone-beam CT. FIG. 4 schematically shows the geometrical relationship between an X-ray irradiation range and a reconstruction area. Of the three slices, a central slice S2 has almost no data omission portion. In two end slices S1 and S3, data omission occurs in most of the peripheral portions indicated by the hatching. As shown in FIG. 5, therefore, in order to prevent image deterioration in the end slices S1 and S3, studies have been made to set the opening degree of the X-ray stop 102 to a slightly large value in accordance with the length of a virtual reconstruction area longer than the actual reconstruction area by a fixed value $\Delta W$.

Image deterioration can be suppressed to some extent by this opening degree setting method. As shown in FIG. 6, however, when the reconstruction area FOV is set to a small radius, areas outside the reconstruction area FOV are excessively irradiated with X-rays, resulting in an increase in X-ray dose.

BRIEF SUMMARY OF THE INVENTION

It is an object of the present invention to prevent both data omission and unnecessary X-ray irradiation in multi-slice CT or cone-beam CT.

An X-ray computed tomography apparatus includes an X-ray tube for generating X-rays diverging in channel and slice directions, an X-ray detector having a plurality of X-ray detection elements for detecting X-rays transmitted through an object to be examined, a rotating mechanism for supporting the X-ray tube and X-ray detector so as to allow them to rotate around the object, a moving mechanism for moving the X-ray tube and X-ray detector relative to the object in the slice direction, a control unit for controlling the rotating mechanism and moving mechanism to execute helical scan operation of acquiring data while making the X-ray tube and X-ray detector rotate around the object and move relative to the object, an input device for setting a substantially cylindrical reconstruction area, and an image reconstructing unit for reconstructing image data within the set reconstruction area on the basis of the output from the X-ray detector. The X-ray computed tomography apparatus also includes a movement distance determining unit for determining the movement distance of the X-ray tube and X-ray detector relative to the object during X-ray generation on the basis of the radius of the set reconstruction area as well as its height.

Additional objects and advantages of the present invention will be set forth in the description which follows, and in part will be obvious from the description, or may be learned by practice of the present invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the present invention and, together with the general description given above and the detailed description of the preferred embodiments given below, serve to explain the principles of the present invention.

FIG. 15 is a block diagram showing the arrangement of an X-ray CT apparatus according to the second embodiment of the present invention;

DETAILED DESCRIPTION OF THE INVENTION

An X-ray computed tomographic imaging apparatus (X-ray CT apparatus) according to a preferred embodiment of the present invention will be described below with reference to the views of the accompanying drawing. Note that X-ray CT scan schemes include various types, e.g., the rotate/rotate type in which an X-ray tube and X-ray detector rotate together around an object to be examined, and the stationary/rotate type in which many detection elements arrayed in the form of a ring are fixed, and only an X-ray tube rotates around an object to be examined. The present invention can be applied to any of these types. In this case, the rotate/rotate type will be exemplified.

The present invention is not limited to an apparatus having only one pair of an X-ray tube and an X-ray detector, and can be applied to a so-called multi-tube type apparatus having a plurality of pairs of X-ray tubes and X-ray detectors mounted at different angles. In this case, an apparatus having one such a pair will be described.

A helical scan is performed by rotating the X-ray tube and detector around an object to be examined while moving them relative to the object. The X-ray tube and detector relative to the object is moved by a scheme of fixing the gantry equipped with the X-ray and detector and moving the top on which the object is placed, a scheme of moving the gantry equipped with the X-ray tube and detector, or a composite scheme thereof. The present invention may use any of these schemes. In this case, the present invention will be described by exemplifying the most typical "scheme of fixing the gantry equipped with the X-ray tube and detector and moving the top on which an object to be examined is placed".

(First Embodiment)

Figure 1:
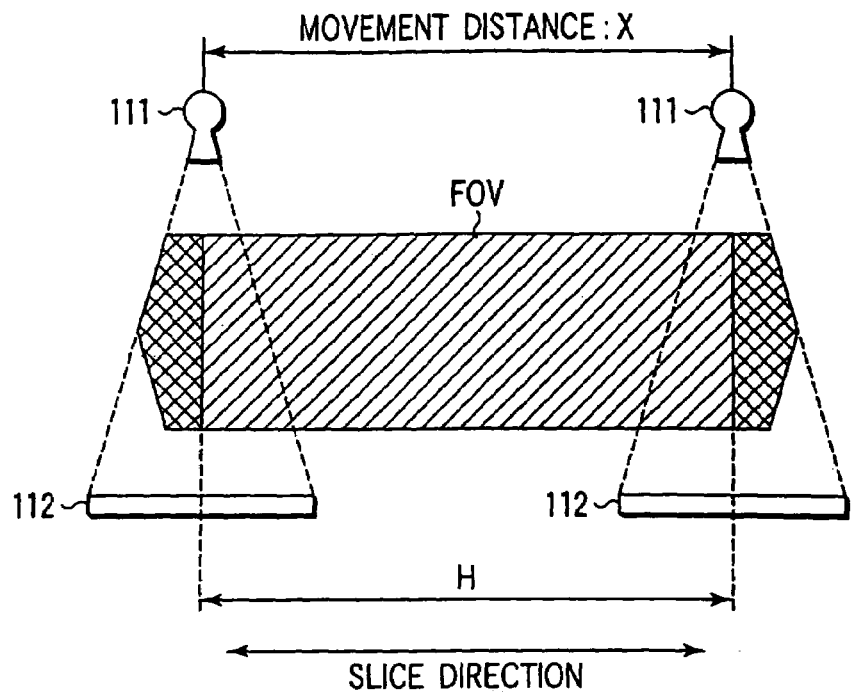
FIG. 1 is a schematic view showing the geometrical relationship between an X-ray irradiation range and a reconstruction area when a helical scan is performed in multi-slice CT or cone-beam CT in the prior art.
Figure 2:
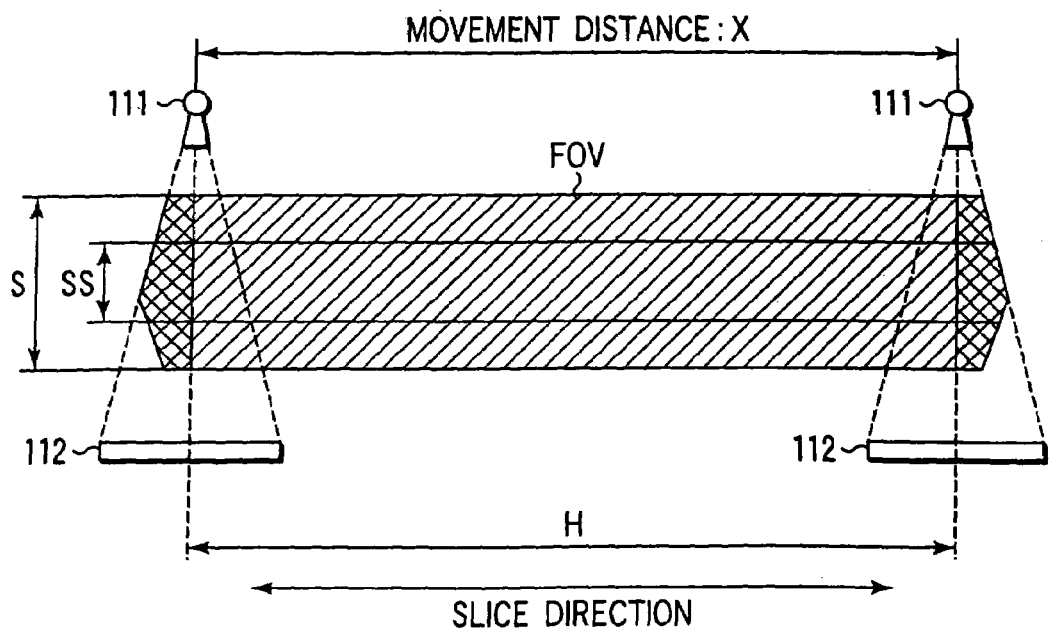
FIG. 2 is a schematic view showing the geometrical relationship between an X-ray irradiation range and a reconstruction area when a helical scan is performed in multi-slice CT or cone-beam CT in the prior art.
Figure 3:
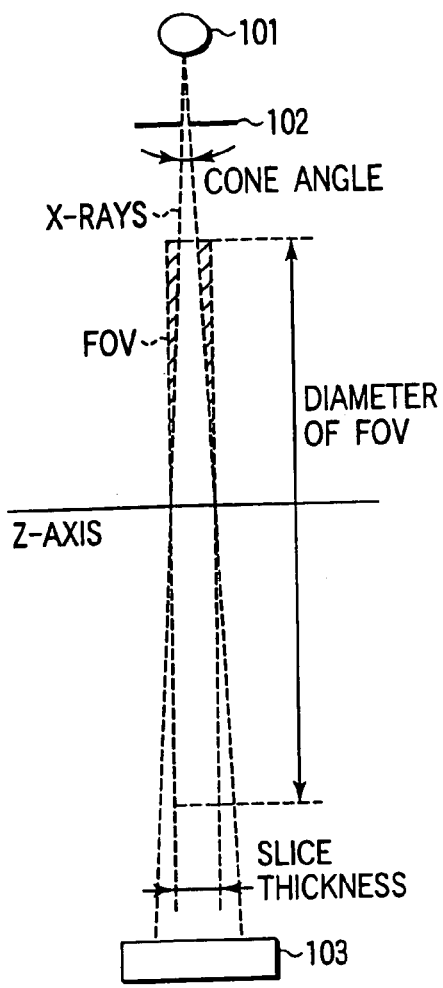
FIG. 3 is a schematic view showing the geometrical relationship between an X-ray irradiation range and a reconstruction area in single-slice TC in the prior art.
Figure 4:
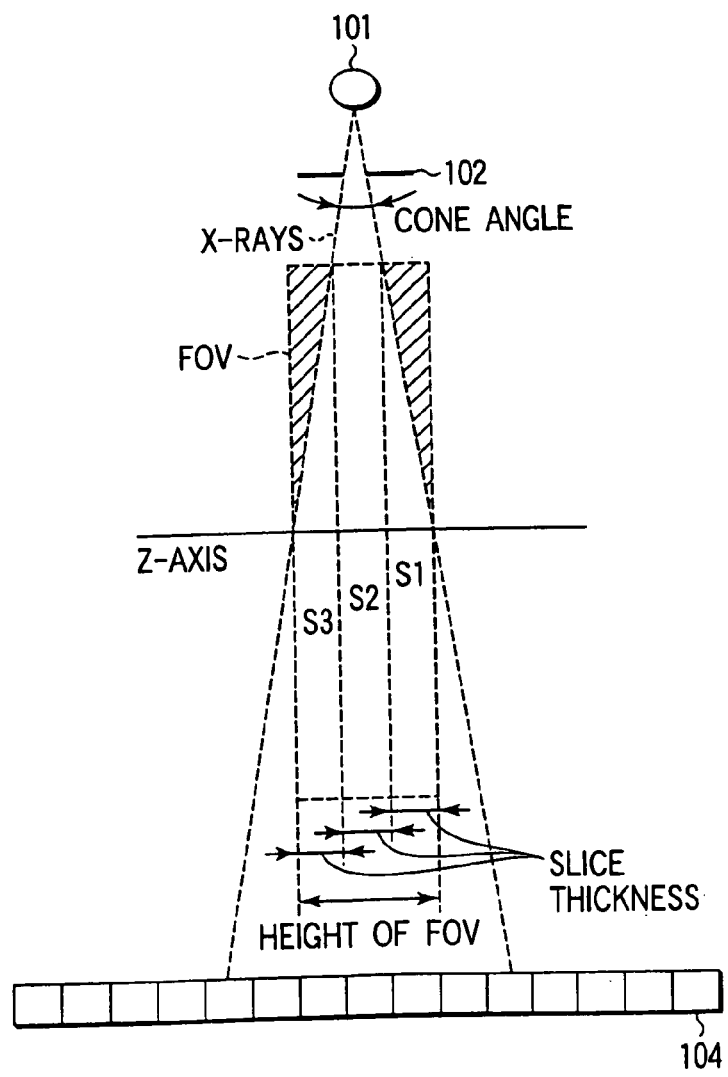
FIG. 4 is a schematic view showing the geometrical relationship between an X-ray irradiation range and a reconstruction area in multi-slice or cone-beam CT in the prior art.
Figure 5:
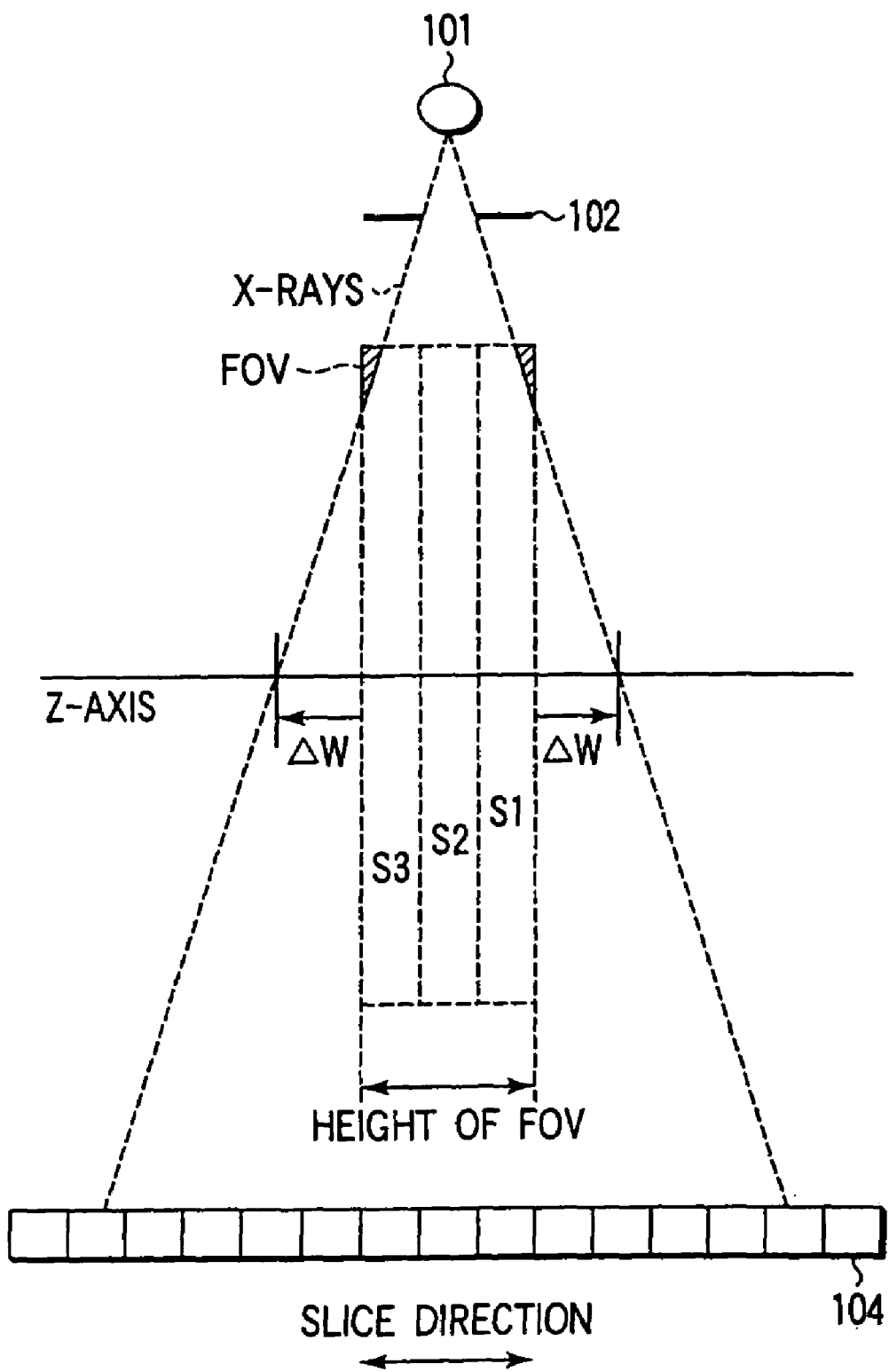
FIG. 5 is a view showing aperture control on a collimator in the prior art.
Figure 6:
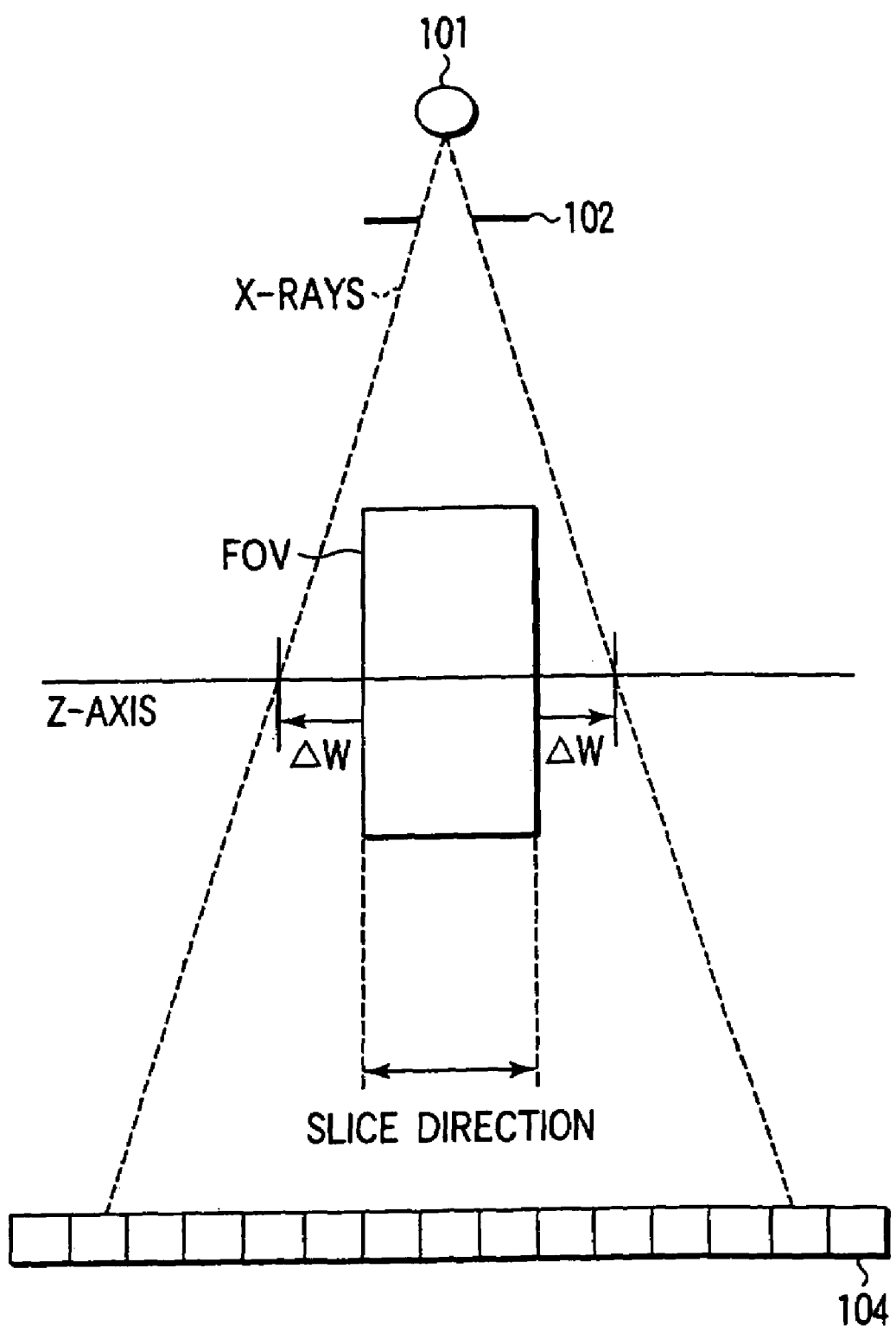
FIG. 6 is a schematic view showing a problem in aperture control on a collimator in the prior art.
Figure 7:
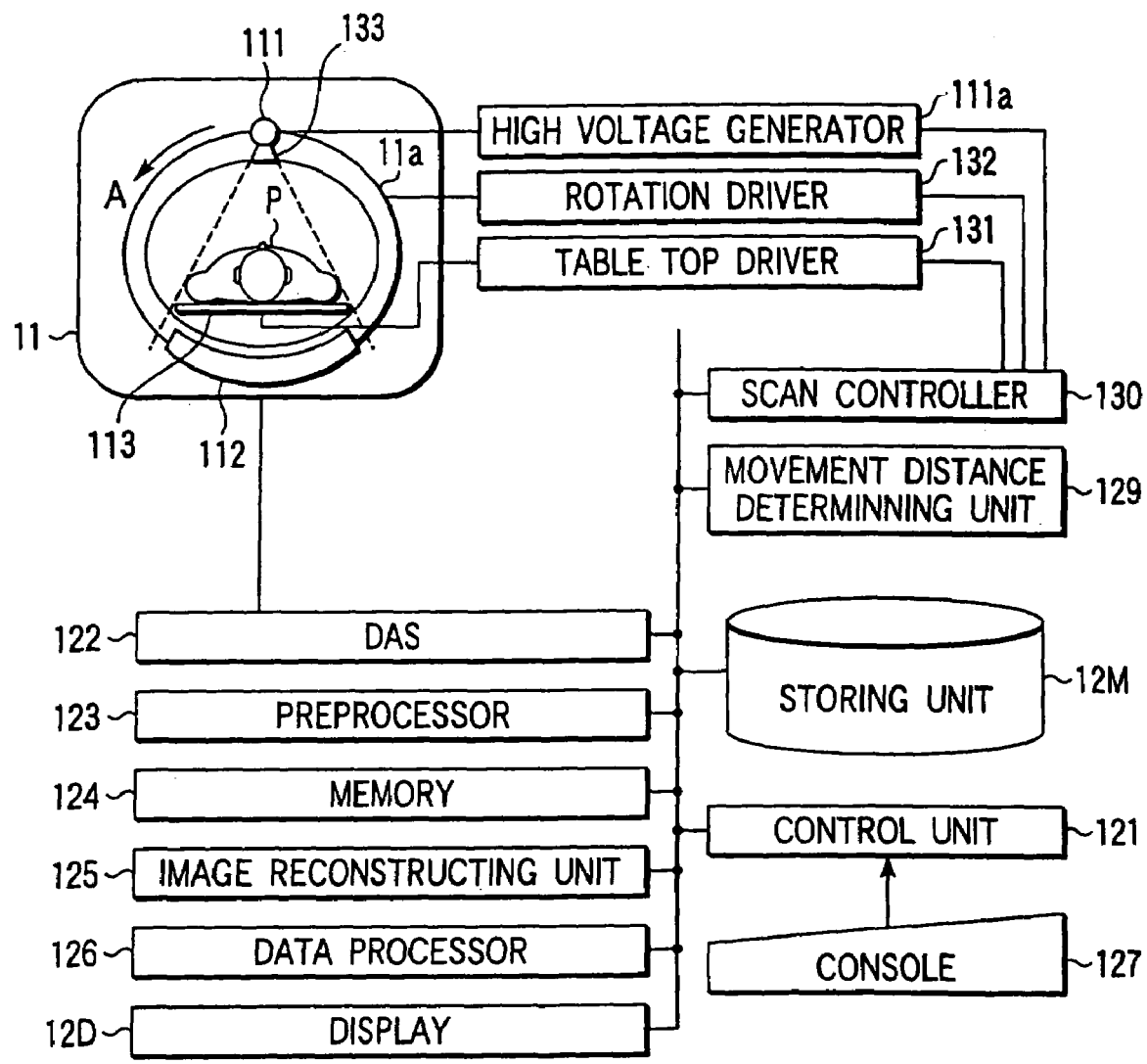
FIG. 7 is a block diagram showing the arrangement of an X-ray CT apparatus according to the first embodiment of the present invention.

FIG. 7 shows an arrangement of an X-ray CT apparatus according to the first embodiment. A gantry 11 has a hollow portion. To scan, an object P to be examined placed on a top 113 of a bed is inserted into the hollow portion. The bed has an electric motor for moving the top 113 upon reception of driving power from a table top driver 131.

The gantry 11 has an X-ray tube 111 and X-ray detector 112. The X-ray tube 111 generates X-rays upon reception of a high voltage from a high voltage generator 111a. The X-ray detector 112 has a plurality of detection elements constituted by, for example, scintillators and photodiodes. The plurality of detection elements are arranged two-dimensionally in the channel and slice directions. For example, M detection elements are arrayed in a line in the channel direction, and N array segments of such detection elements are arrayed along the slice direction.

The X-ray tube 111 and X-ray detector 112 are rotatably supported by a rotating mechanism 11a. The rotating mechanism 11a has an electric motor for rotating the X-ray tube 111 and X-ray detector 112 upon reception of driving power from a rotation driver 132.

A collimator 133 is attached to the X-ray radiation window of the X-ray tube 111. The collimator 133 has a plurality of shield plates to limit the divergence angle (fan angle) of X-rays from the X-ray tube 111 in the channel direction and the divergence angle (cone angle) of the X-rays in the slice direction, and electric motors for separately moving the shield plates to separately change the fan angle and cone angle.

Figure 8A:
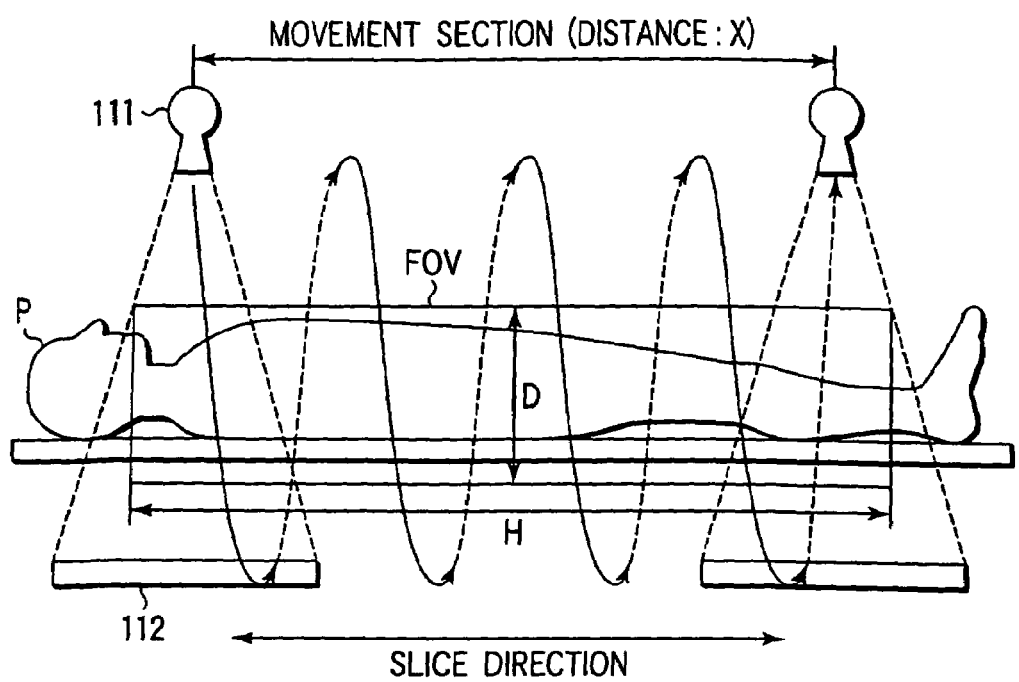
FIGS. 8A and 8B are views showing a reconstruction area in the first embodiment.
Figure 8B:
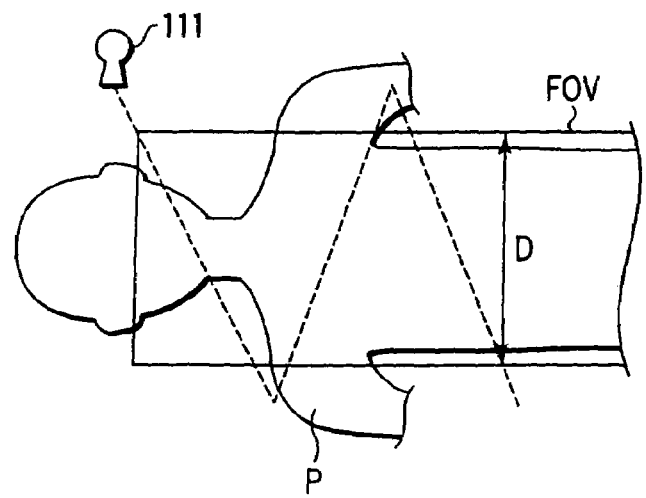

As the X-ray tube 111 and X-ray detector 112 rotate, the top 113 on which the object P is placed continuously moves along the body axis direction (slice direction) of the object P. With this operation, as shown in FIGS. 8A and 8B, the X-ray tube 111 moves relative to the object along a helical path.

Figure 9:
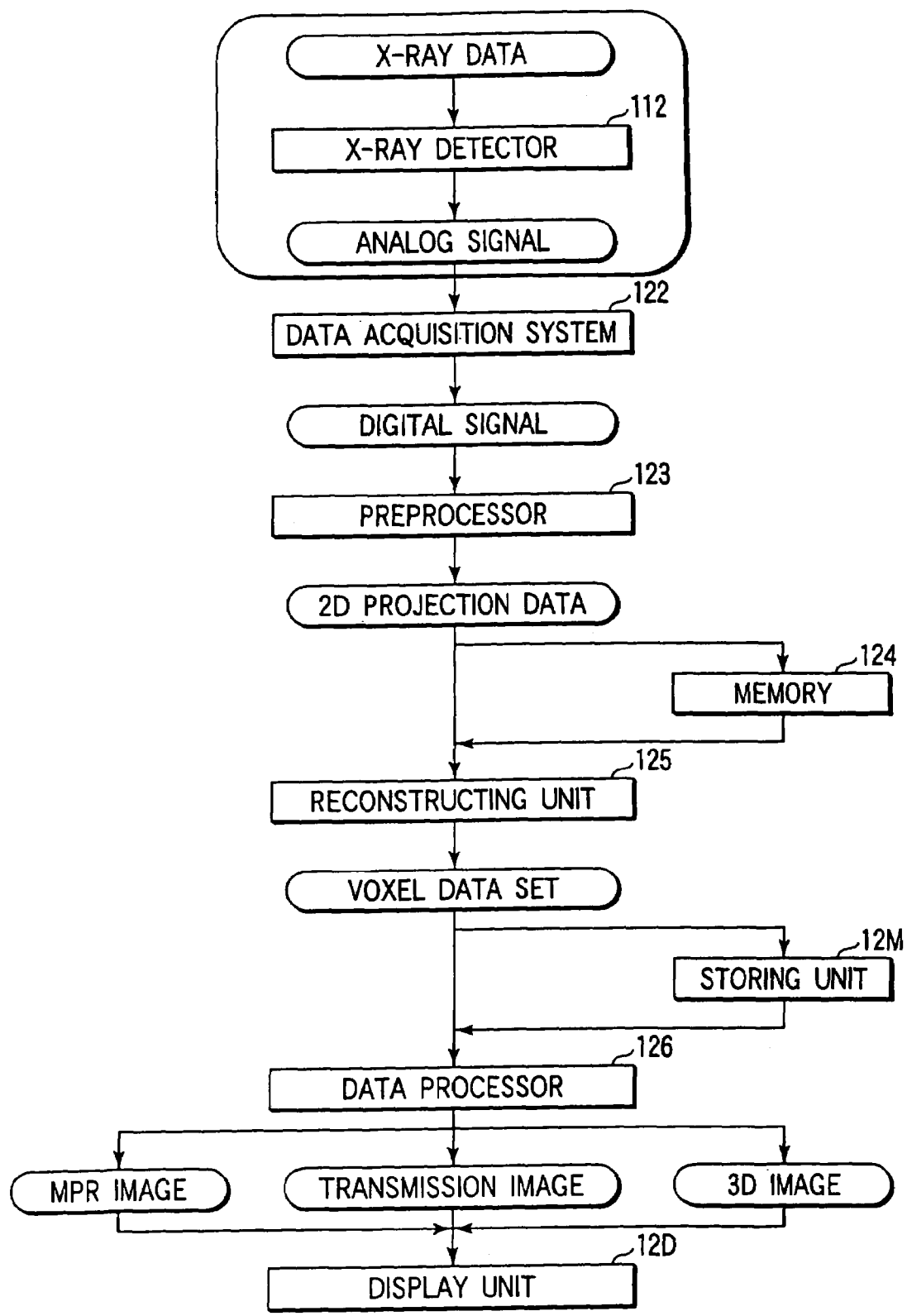
FIG. 9 is a view showing the flow of data in the first embodiment.

As shown in FIG. 9, the data (raw data) detected by the X-ray detector 112 is amplified by a data acquisition system (DAS) 122 and converted into digital data. Note that the data output from the DAS 122 will be referred to as raw data. A preprocessor 123 executes preprocessing such as sensitivity correction and X-ray intensity correction for the raw data. Note that the data having undergone the preprocessing will be referred to as "projection data". A memory 124 stores the projection data. An image reconstructing unit 125 receives the projection data from the memory 124 and reconstructs 3D distribution data of CT values which relatively represent an X-ray absorption coefficient on the basis of this projection data. Typically, for reconstruction processing, the Feldkamp method is used. The 3D distribution data of CT values is sent to a data processor 126 directly or via a storing unit 12M. The data processor 126 generates MPR image data of an arbitrary slice or transmission image data or 3D image data from an arbitrary direction on the basis of the 3D distribution data of CT values. The display 12D displays an image on the basis of MPR image data or the like. The storing unit 12M stores the data (image data) about the MPR image reconstructed in this manner, the above projection data, the above CT value data set, and the like. For example, as this storing unit, a known hard disk or the like may be used.

A console 127 includes a pointing device such as a mouse or trackball, a keyboard, a touch panel display, a GUI controller for generating graphical user interface data displayed on the touch panel display, and the like.

Scan conditions, reconstruction conditions, and the like are input through the console 127. The scan conditions include a tube voltage, tube current, scan cycle (rotation time), helical pitch (movement distance of the top 113 per rotation), the movement start position of the top 113, the movement end position of the top 113, cone angle (the number of arrays of segments used), and the like. The reconstruction conditions include the radius and height of the reconstruction area FOV, the number of slices, slice thickness, slice pitch, and the like.

A movement distance determining unit 129 determines the movement distance of a helical scan on the basis of the radius and height of the reconstruction area FOV which are set through the console 127. This determination method will be described later. A scan controller 130 controls the high voltage generator 111a, rotation driver 132, table top driver 131, and the like to execute a helical scan in accordance with the set tube voltage, tube current, scan cycle (rotation time), scan pitch, and the like.

Note that the arrangement of the X-ray CT apparatus shown in FIG. 7 is only an example. For example, in the arrangement in FIG. 7, the image reconstructing unit 125 and the like are incorporated in the computer unit separate from the gantry 11. However, the image reconstructing unit 125 and the like may be mounted in the gantry 11. Alternatively, the DAS 122 may be mounted in the gantry 11, and the preprocessor 123 and the like may be incorporated in the computer unit. In this arrangement, electrical signals may be transmitted from the former to the latter by using a noncontact data transmission means (not shown). That is, the present invention is not specifically limited to such arrangements.

Figure 10:
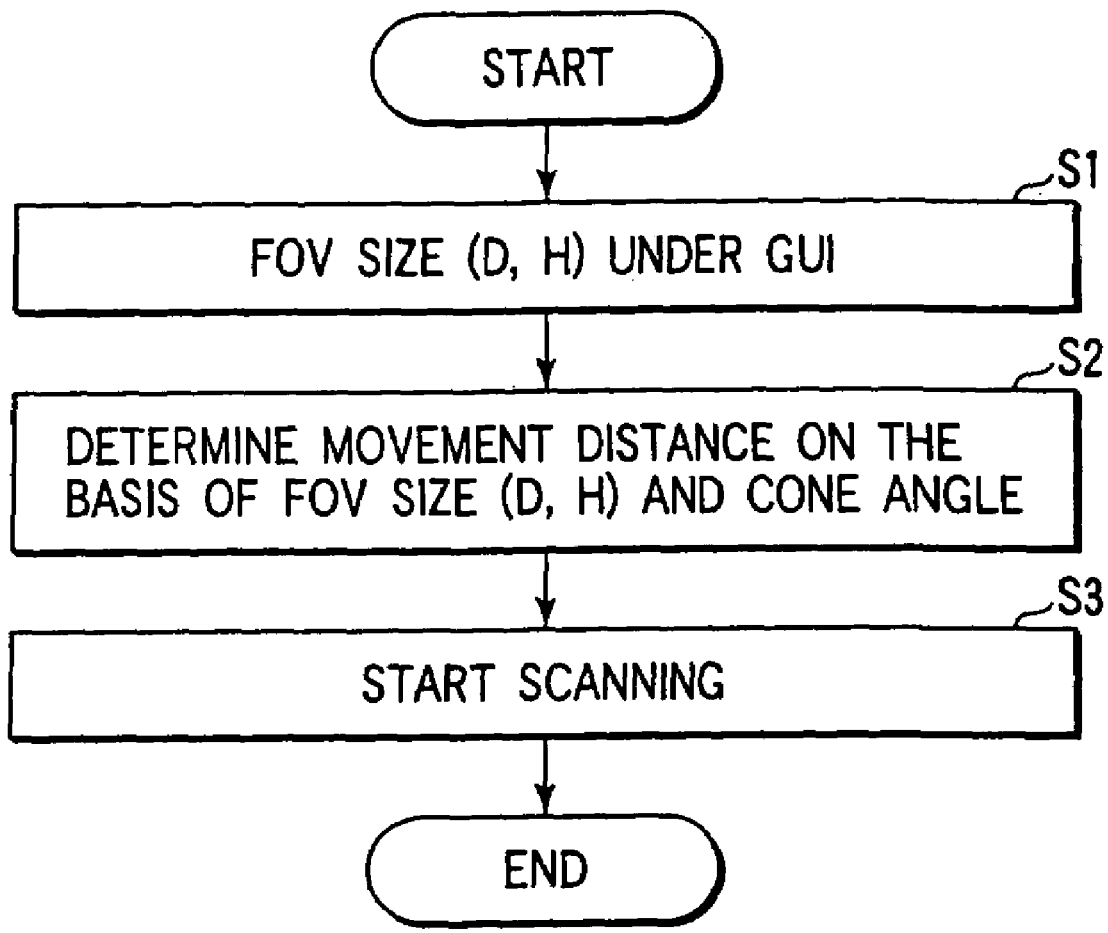
FIG. 10 is a flow chart showing the flow of movement distance determination processing in the first embodiment.
Figure 11:
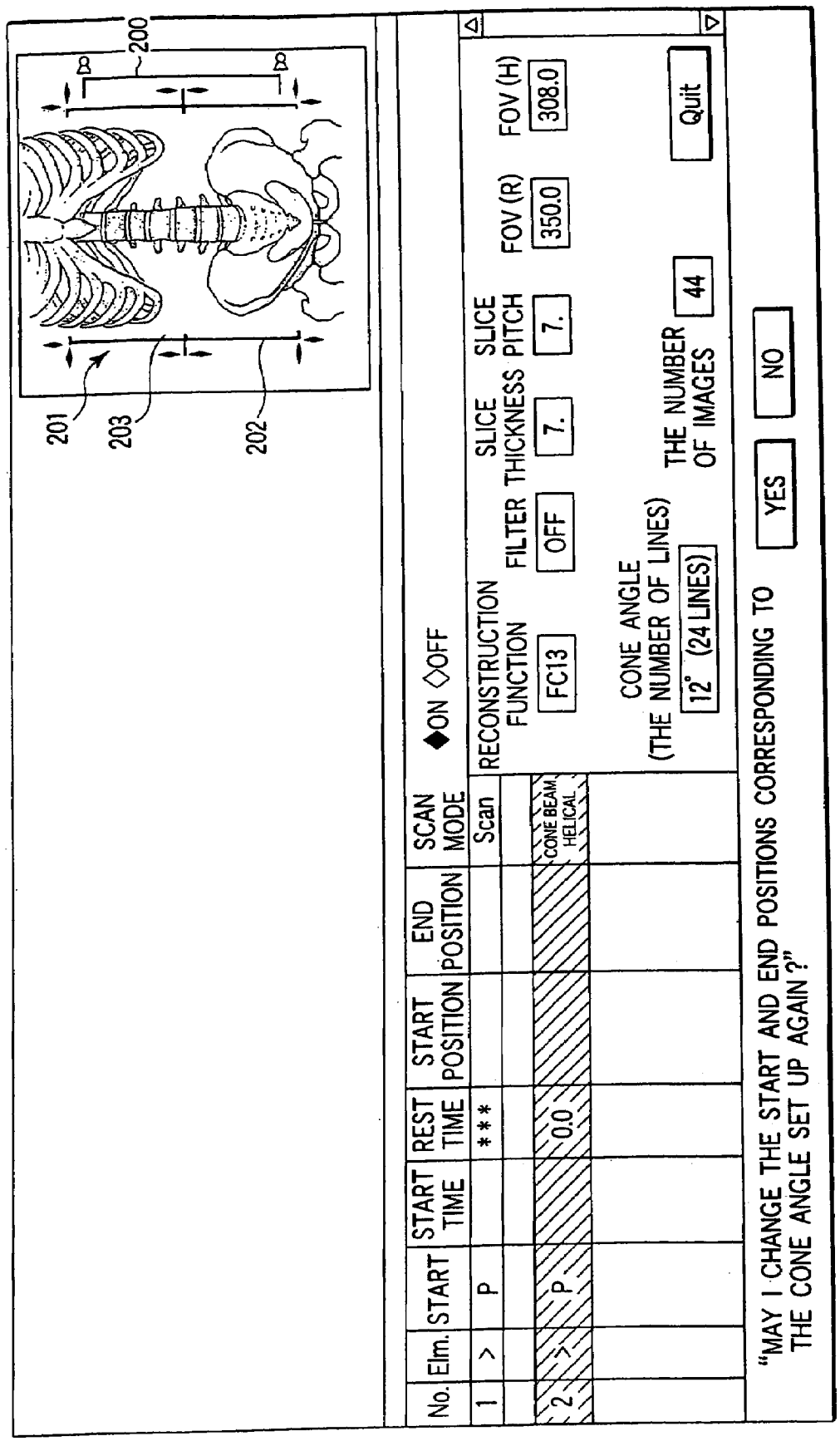
FIG. 11 is a view showing a GUI for scan condition setting which is provided by an input unit in FIG. 7.

FIG. 10 shows the flow of processing, from preparations for a helical scan to execution thereof. In step S1, the size of the cylindrical reconstruction area FOV, i.e., a radius D and height H, are set. As shown in FIG. 8B, the reconstruction area FOV is determined by the body thickness and width of the object P. To support setting of the reconstruction area FOV, the expert function of the console 127 provides the graphical interface shown in FIG. 11. This graphical interface includes a scanogram 201. A frame line 202 and center line 203 of the reconstruction area FOV are synthesized with the scanogram 201. The user arbitrarily changes the width and length of the frame line 202 or arbitrarily moves the center line 203 by operating a pointing device or the like. In addition, a mark 200 indicting the movement range of the gantry 11 is synthesized with the scanogram 201. The graphical interface also includes a numerical value input window for a slice thickness, slice pitch, helical pitch, the number of images, the radius D of the reconstruction area FOV, the height H of the reconstruction area FOV, and cone angle. The cone angle may be calculated based on the input slice thickness and the input number of slices. The radius D and height H of the reconstruction area FOV are linked with the size of the frame line 202 of the reconstruction area FOV on the scanogram 201.

The movement distance determining unit 129 then determines the movement section (movement start position, movement end position, and movement distance) of the X-ray tube 111 relative to the object P on the basis of the set radius D and height H of the reconstruction area FOV.

In this case, a movement section is defined as a section in which the X-ray tube 111 moves relative to an object to be examined, with X-ray generation and data acquisition. A section in which the X-ray tube 111 moves without X-ray generation and data acquisition is defined as a free movement section to be discriminated from the movement section.

Figure 12A:
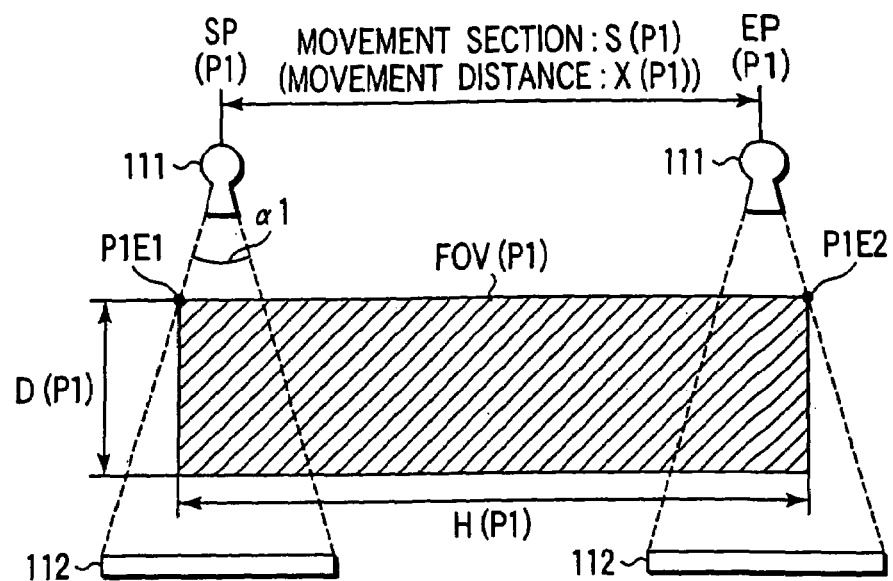
FIGS. 12A and 12B are views showing the relationship between the radius of a reconstruction area and a movement distance in the first embodiment.

FIG. 12A shows a movement section S (P1) of the X-ray tube 111 relative to the object P which is determined on the basis of a set cone angle $\alpha 1$ and a set radius D (P1) and height H(P1) of a reconstruction area FOV (P1).

A start position SP(P1) of the movement section S (P1) is set at the position where one end ray of X-rays diverging at the cone angle $\alpha 1$ comes into contact with an edge P1E1 of one end face of the reconstruction area FOV (P1). An end position EP (P1) of the movement section S(P1) is set at the position where the other end ray of the X-rays diverging at the cone angle $\alpha 1$ comes into contact with an edge P1E2 of the other end face of the reconstruction area FOV (P1). In other words, the start and end positions are determined to the positions that satisfy the conditions that the edges P1E1 and P1E2 are located on the ridgelines of the X-ray beam defined by the cone angle $\alpha 1$. A distance X (P1) of the movement section S(P1) is determined to the distance between the start position SP(P1) and the end position EP (P1). The movement section S is the standard section to decide an actual movement section. Expansion sections corresponding to the reconstructing method and the interpolating method are added on both sides of the standard movement section S. The section where expansion sections are added to the standard movement section S is set up as an actual movement section.

The position and length of the mark 200 indicating a movement range on the scanogram 201 are changed in accordance with the determined movement section S(P1).

Figure 12B:
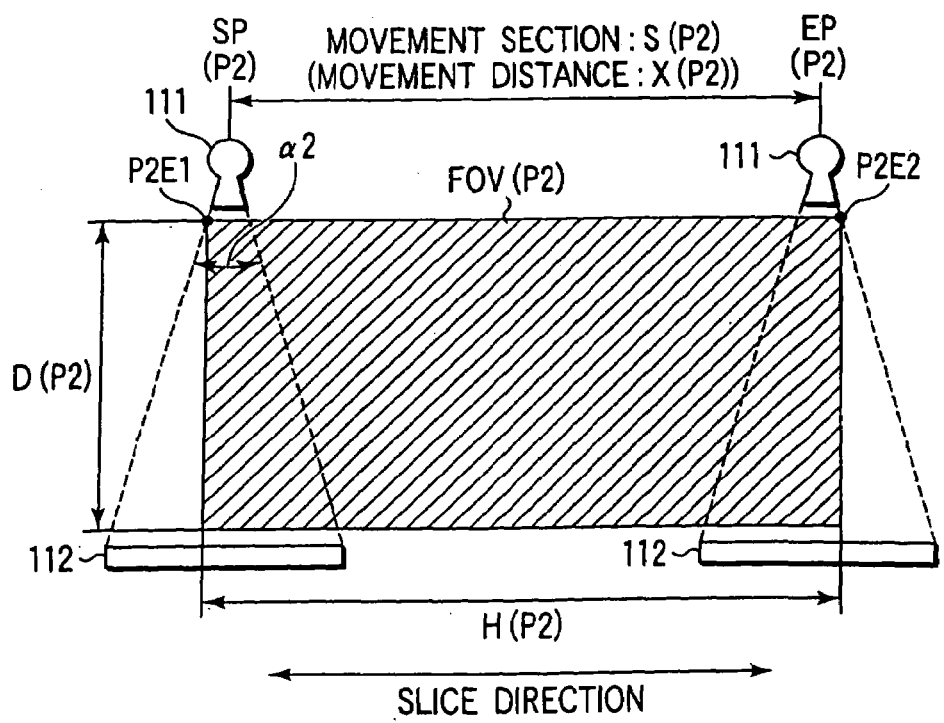

As shown in FIG. 12B, when the cone angle is set to $\alpha 2$ and a reconstruction area FOV (P2) is set to a radius D (P2) and height H(P2), a start position SP (P2) of the movement section S(P2) is determined to the position where one end ray of X-rays diverging at the cone angle $\alpha 2$ comes into contact with an edge P2E1 of one end face of the reconstruction area FOV (P2). An end position EP (P2) of the movement section S(P2) is determined to the position where the other ray of the X-rays diverging at the cone angle $\alpha 2$ comes into contact with an edge P2E2 of the other end face of the reconstruction area FOV (P2). A distance X (P2) of the movement section S(P2) is determined to the distance between the start position SP(P2) and the end position EP (P2). According to this determination method, the distance X (P2) of the movement section S(P2) is always determined to a distance shorter than the height H(P2) of the reconstruction area FOV (P2).

In helical scan operation (S3), the X-ray tube 111 and X-ray detector 112 rotate under the control of the scan controller 130, while the X-ray tube 111 moves at a constant speed corresponding to a helical pitch, relative to the object P, from the start position SP to the end position EP of the movement section S. In practice, the top 113 moves.

X-rays are generated continuously or in the form of pulses while the X-ray tube 111 moves relative to the object P from the start position SP to the end position EP of the movement section S, thereby acquiring data.

Figure 13:
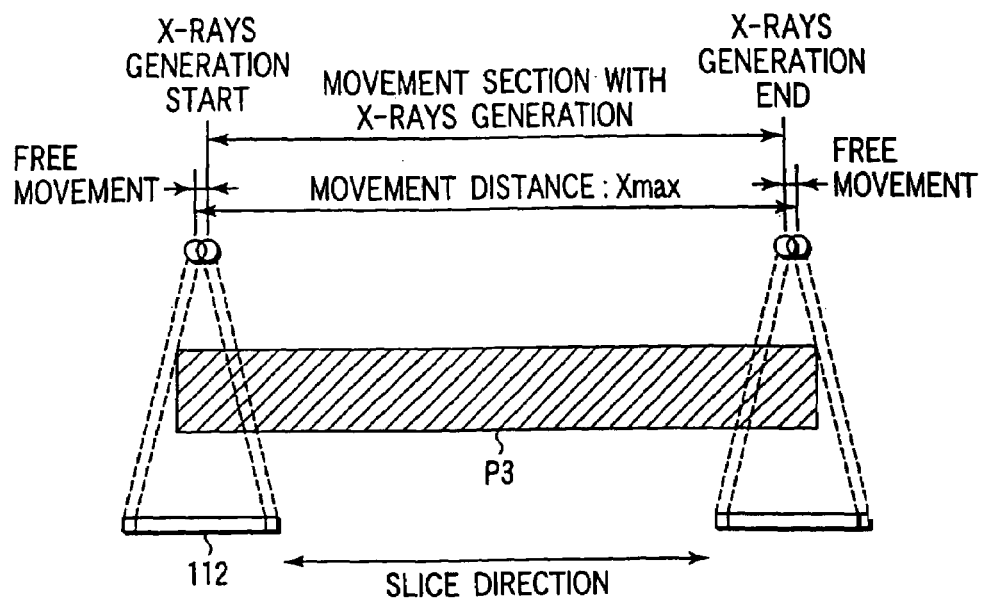
FIG. 13 is a supplementary view for defining a movement distance in the first embodiment.

Assume that the section in which the X-ray tube 111 moves relative to an object to be examined is set to be loner than the movement section determined above. In this case, as shown in FIG. 13, X-ray generation and data acquisition are started when the X-ray tube 111 moves to the start position of the movement section, and are stopped when the X-ray tube 111 moves to the end position of the movement section. Free movement without X-ray generation and data acquisition is performed in sections before and after the start and end positions.

In this manner, data omission and unnecessary X-ray generation can be prevented by determining the movement section (movement start position, movement end position, and movement distance) of the X-ray tube 111 relative to the object P on the basis of a set cone angle and the set radius D and height H of the reconstruction area FOV.

As described above, in this embodiment, a movement section is determined in accordance with a cone angle and the radius and height of the reconstruction area FOV. If, therefore, the cone angle and the radius and height of the reconstruction area FOV are changed, the movement section also changes accordingly. When the movement section changes, the cone angle may have to be changed in order to maintain the radius or height of the reconstruction area FOV. In such a case, the expert function of the console 127 displays, for example, the message shown in FIG. 11 "May I change the start and end positions corresponding to the cone angle set up again?" on the graphical interface. This message assures that the user will set up a cone angle again approving a change in the movement section.

(Second Embodiment)

The first embodiment described above relates to the technique of preventing data omission and unnecessary X-ray generation in a helical scan in multi-slice or cone-beam CT. The second embodiment relates to a technique of preventing data omission and unnecessary X-ray generation in a conventional scan in multi-slice or cone-beam CT.

Figure 14:
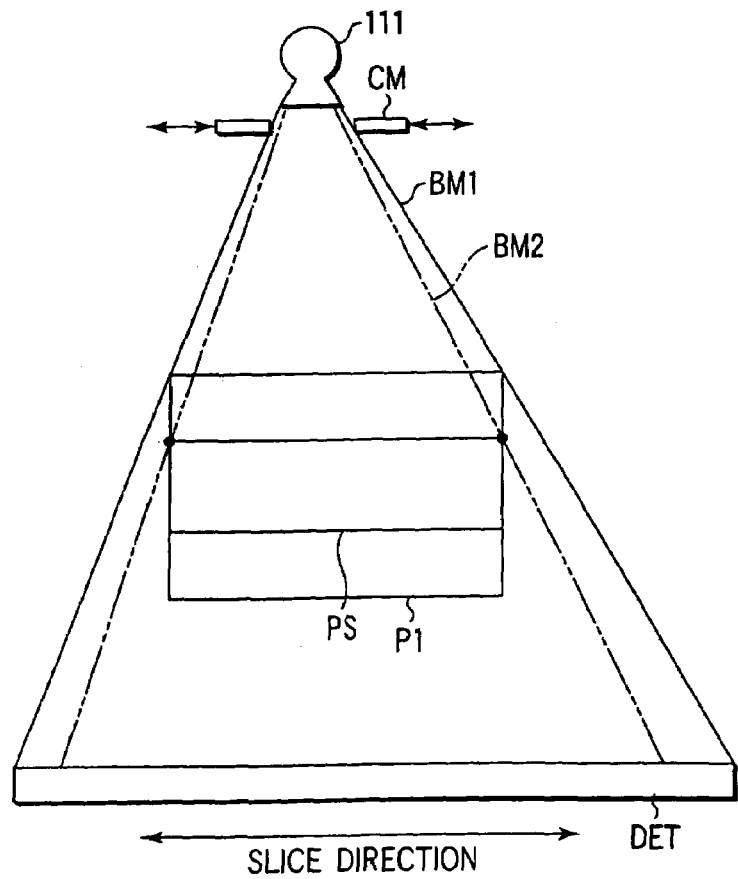
FIG. 14 is a view showing an outline of the second embodiment of the present invention.

A conventional scan is a scan that is performed to acquire data while an X-ray tube is fixed relative to an object to be examined. For example, as shown in FIG. 14, many arrays (e.g., 600 arrays) of X-ray detectors DET are arranged in the body axis direction to oppose an X-ray tube 111. Multi-slice data are acquired by rotating these X-ray detectors around a object P to be examined while a wide-angle cone beam (with large cone and fan angles) is radiated from the X-ray tube 111. Assume that the cone angle is fixed, and a reconstruction area P1 with a large radius is to be scanned. In this case, no data omission occurs, and the object is not irradiated with unnecessary X-rays. If, however, a reconstruction area PS with a smaller radius is scanned, the object is irradiated with unnecessary X-rays although no data omission occurs. In contrast to this, if a reconstruction area having a larger radius than the area P1 is scanned, data omission occurs.

Figure 16:
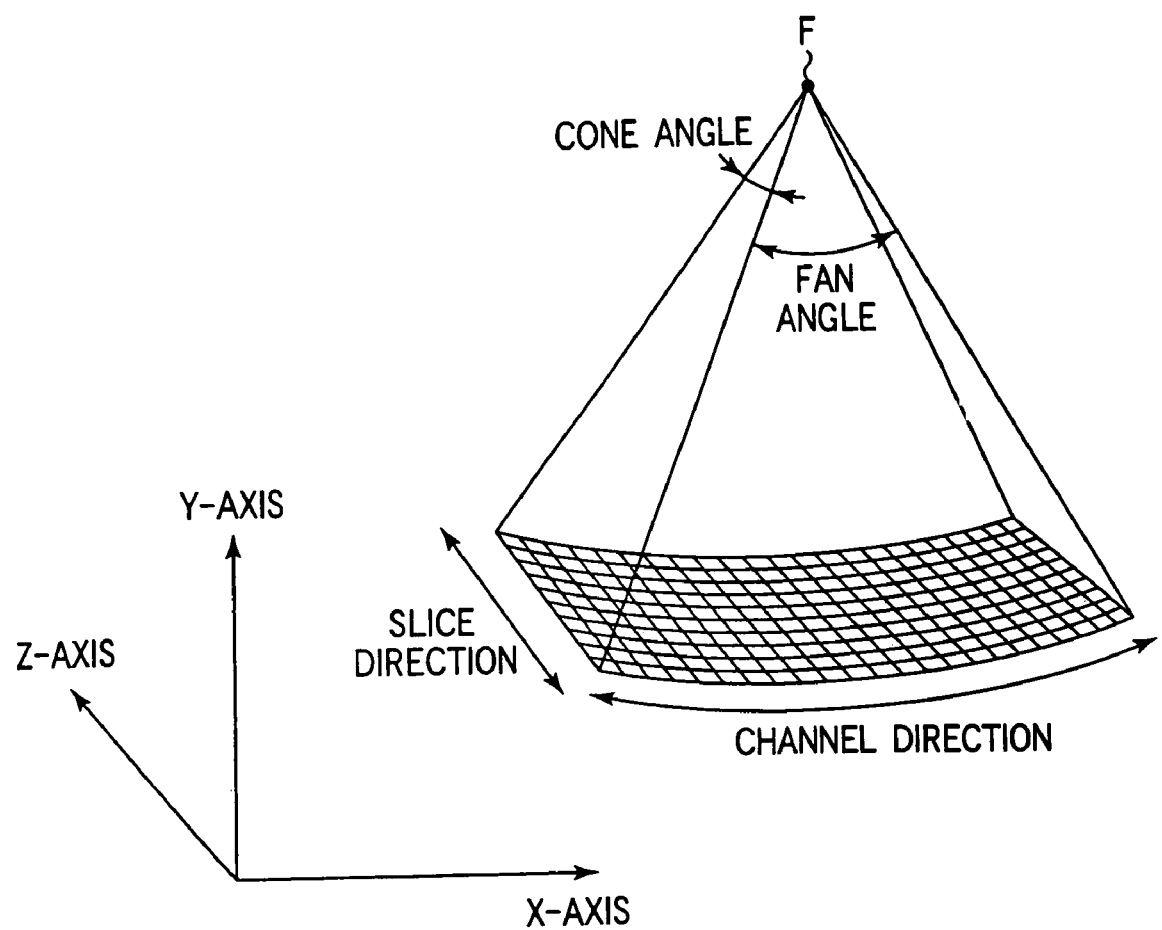
FIG. 16 is a perspective view of a detector in FIG. 15.

FIG. 15 shows the arrangement of an X-ray computed tomographic imaging apparatus according to the second embodiment. An X-ray tube 31 and X-ray detector 34 are rotatably supported by a rotating mechanism and spaced apart from each other by a distance required to ensure a space in which the object P on a top 33 is inserted. The X-ray detector 34 is defined as an X-ray detector having a function of simultaneously acquiring the projection data of a plurality of slices. Typically, as shown in FIG. 16, this detector has a structure in which arrays of detection elements arranged in the channel direction, i.e., segments, are coupled to each other in the slice direction, or n x m arrays of detection modules are coupled to each other in the two directions, i.e., the channel and slice directions, or in one direction, i.e., the channel direction.

A collimator (to be also referred to as an X-ray stop unit) 32 is mounted at the front surface of the X-ray radiation window of the X-ray tube 31. The collimator 32 is designed to separately change the opening degree in the channel direction and the opening degree in the slice direction. Typically, the collimator 32 is comprised of a plurality of X-ray shield plates, a mechanism for movably holding each X-ray shield plate, and an X-ray shield plate driving unit for separating moving the X-ray shield plates by using electric motors. The fan angle of X-rays is limited by the opening degree of the collimator 32 in the channel direction, and the cone angle of the X-rays is limited by the opening degree of the collimator 32 in the slice direction.

A signal having a peak value corresponding to the intensity of an X-ray output from each channel of the X-ray detector 34 is acquired by a data acquisition section (which is commonly called a DAS) 35 via, for example, a slip ring. The data acquisition section 35 separately amplifies detection signals on a channel basis, converts them into digital signals, and outputs them as projection data to an image reconstructing unit 41. The data acquisition section 35 may amplify detection signals on a plurality of channels as a whole and convert them into digital data. The image reconstructing unit 41 reconstructs MPR image data in a multi-slice form on the basis of the projection data. This MPR image data is displayed on a display/console 42 and sent to a storing unit 40 to be stored in a large-capacity storage medium such as a magnetooptical disk unit.

A series of operations including data acquisition, reconstruction, image display, and storage are performed under the control of a computer 39. In addition to these signal processing control operations, the computer 39 controls setting of scan environments for the apparatus in accordance with the imaging conditions set through the display/console 42 and functions as a control center for the overall apparatus including the gantry controller and the like during a scan.

The imaging conditions set by the operator through the display/console 42 include the width (radius or radius; radius in this case) of a cylindrical reconstruction area FOV having a thickness, slice thickness, and the number of slices, in addition to a tube voltage, tube current, scan time, and the like. Note that the size of the reconstruction area FOV is defined by the above radius and a height. In multi-slice CT, the height of the reconstruction area FOV is determined by slice thickness x slice count.

The computer 39 supplies the data of the set tube voltage and tube current to an X-ray control unit 37. The X-ray control unit 37 controls a high voltage generator 36 to radiate X-rays from the X-ray tube 31 at this tube voltage and tube current. The computer 39 supplies the data of the set scan time to a gantry controller 38. The gantry controller 38 controls an electric motor serving as a rotating mechanism to rotate the X-ray tube 31 once around an object to be examined in the scan time.

The computer 39 also supplies the data of the set radius and height of the reconstruction area FOV to the gantry controller 38. The gantry controller 38 controls the X-ray shield plate driving unit of the collimator 32 to match the opening degree of the collimator 32 in the slice direction with a distance corresponding to the radius and height of the reconstruction area FOV.

Figure 17:
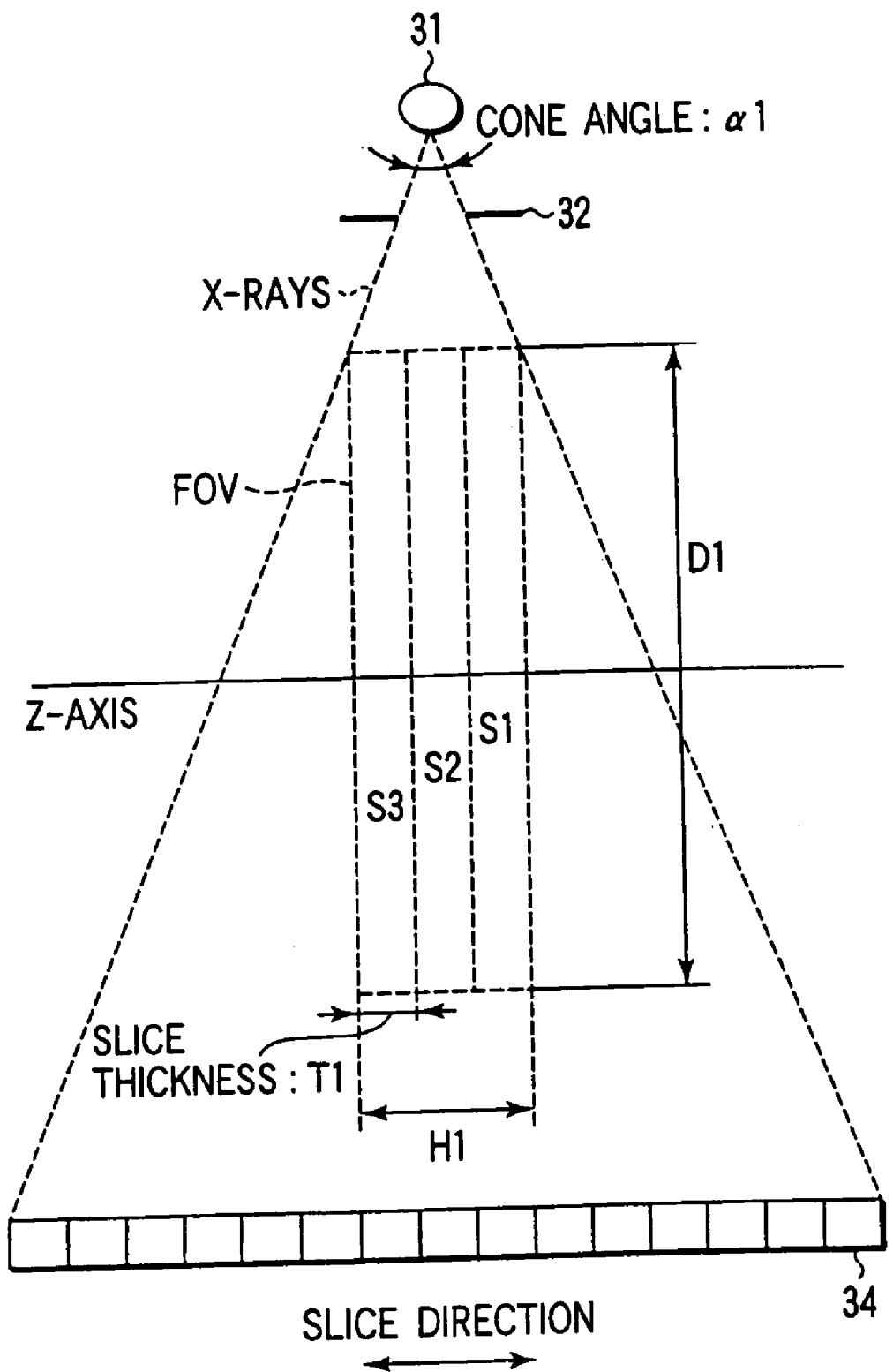
FIG. 17 is a view showing a cone angle α1 determined in accordance with the size (radius Dl and height Hl) of a reconstruction area in the second embodiment.
Figure 18:
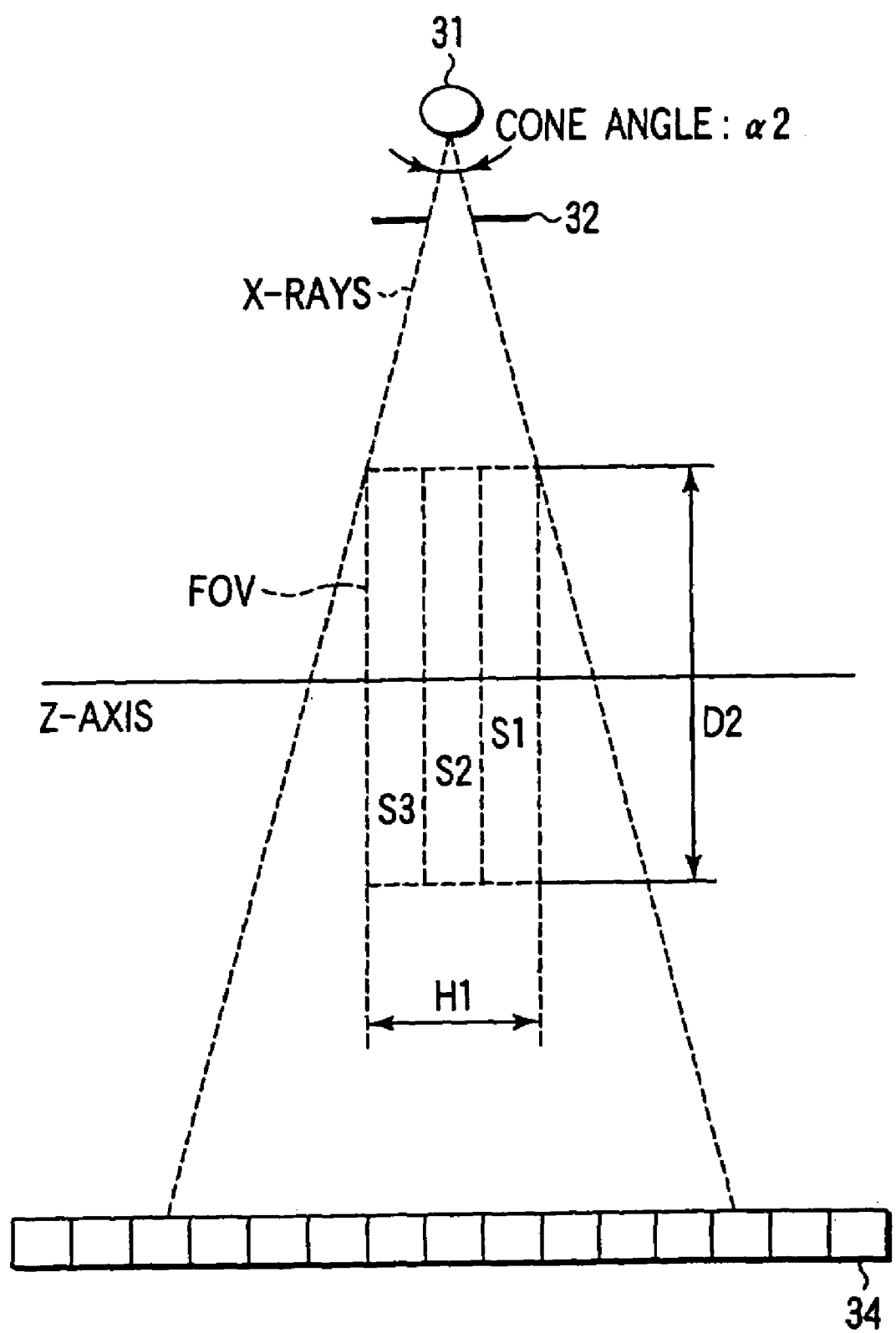
FIG. 18 is a view showing a cone angle α2 determined in accordance with the size (radius D2 and height Hl) of a reconstruction area in the second embodiment.
Figure 19:
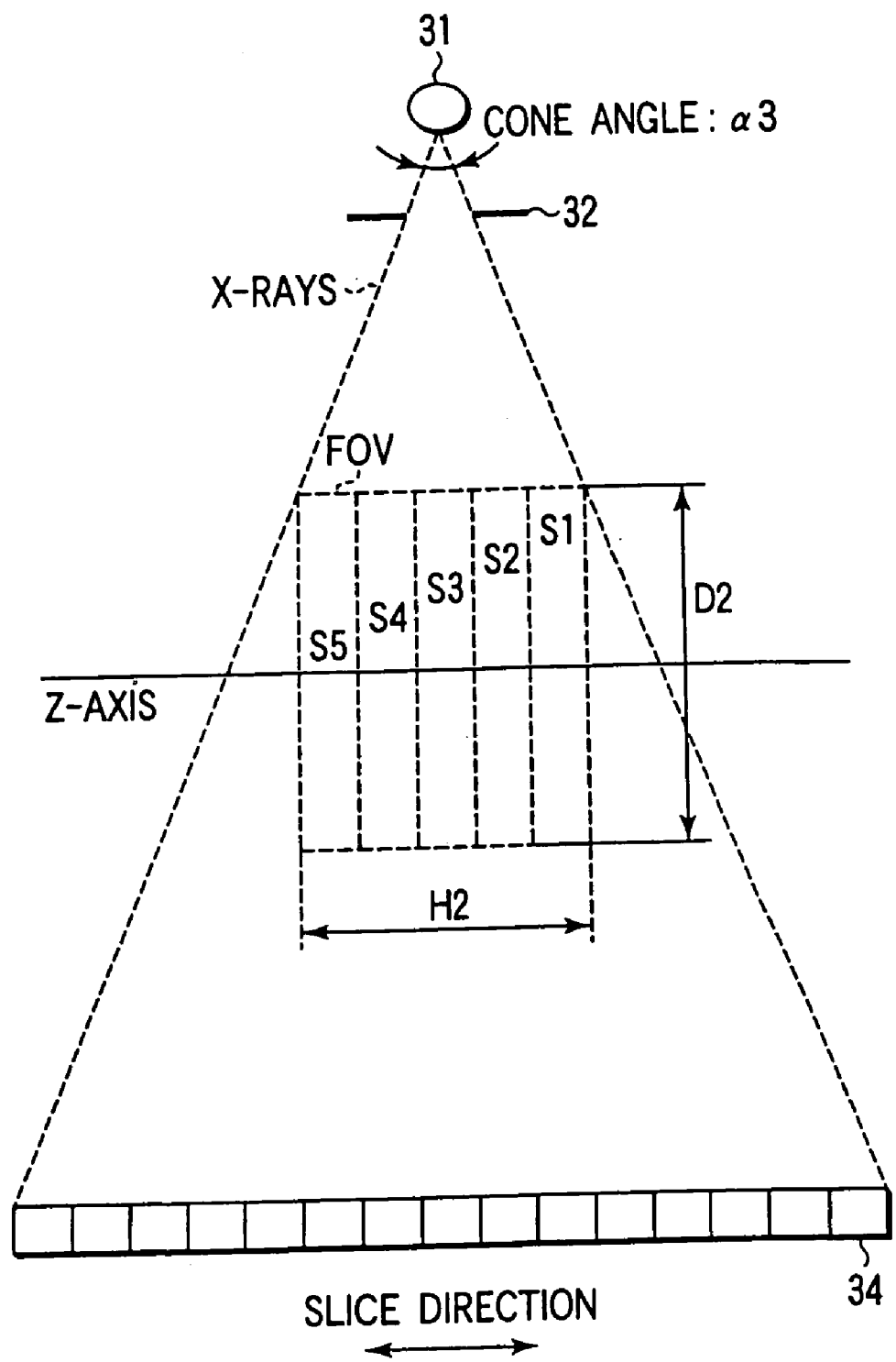
FIG. 19 is a view showing a cone angle α3 determined in accordance with the size (radius D2 and height H2) of a reconstruction area in the second embodiment.

FIG. 17 shows the opening degree of the collimator 32 and a cone angle α1 when the radius and height of the reconstruction area FOV are set to D1 and H1, respectively. FIG. 18 shows the opening degree of the collimator 32 and a cone angle α2 when the radius and height of the reconstruction area FOV are set to D2 (D2<Dl) and Hi, respectively. FIG. 19 shows the opening degree of the collimator 32 and a cone angle α3 when the radius and height of the reconstruction area FOV are set to D2 (D2<Dl) and H2 (H2>H1), respectively. According to the prior art, the opening degree (cone angle) of the collimator 32 is so adjusted as to match the thickness of an X-ray beam with the height H of the reconstruction area FOV on the rotational center axis. This causes data omission.

In contrast to this, according to this embodiment, the opening degree of the collimator 32 and a cone angle are determined on the basis of the radius of the reconstruction area FOV as well as the height H of the reconstruction area FOV. More specifically, the opening degree (cone angle) of the collimator 32 is determined such that the reconstruction area FOV is entirely irradiated with X-rays. More specifically, the opening degree (cone angle) of the collimator 32 is determined such that the thickness of an X-ray beam in the slice direction coincides with the height H of the reconstruction area FOV at a position closer to the X-ray tube 31 than the rotational center axis by the radius of the reconstruction area FOV.

In other words, the opening degree (cone angle) of the collimator 32 is determined such that one end ray of X-rays comes into contact with an edge of one end face of the reconstruction area FOV and the other end ray of the X-rays comes into contact with an edge of the other end face of the reconstruction area FOV.

This makes it possible to prevent data omission throughout the reconstruction area FOV, i.e., acquire projection data throughout the reconstruction area FOV. No image deterioration due to data omission therefore occurs in end slices S1 and S3 as well as a central slice S2. In addition, since no X-ray is radiated outside the reconstruction area FOV, the X-ray dose can be minimized.

According to a preferred implementation method, a table designed to input the radius and height of the reconstruction area FOV and output the corresponding opening degree of the collimator 32 is stored in a ROM, and the ROM is incorporated in the gantry controller 38 (or computer 39). Obviously, however, the gantry controller 38 (computer 39) may obtain the opening degree of the collimator 32 by a geometrical calculation on the basis of two parameters, i.e., the radius and height of the reconstruction area FOV.

Note that the cone angle of X-rays has its upper limit depending on the width of the X-ray detector 34 in the slice direction. More specifically, assume that the reconstruction area FOV is set to a relatively large size. In this case, if the opening degree of the collimator 32 is so adjusted as to irradiate the entire reconstruction area FOV with X-rays, the X-ray irradiation field exceeds the sensitivity area of the X-ray detector 34 in the slice direction. In order to prevent such a situation, in the gantry controller 38, the opening degree at which the X-ray irradiation field coincides with the sensitivity area of the X-ray detector 34 in the slice direction is set as a limiter on control for the collimator 32, or the movement range of the shield plates of the collimator 32 is physically limited.

Figure 20:
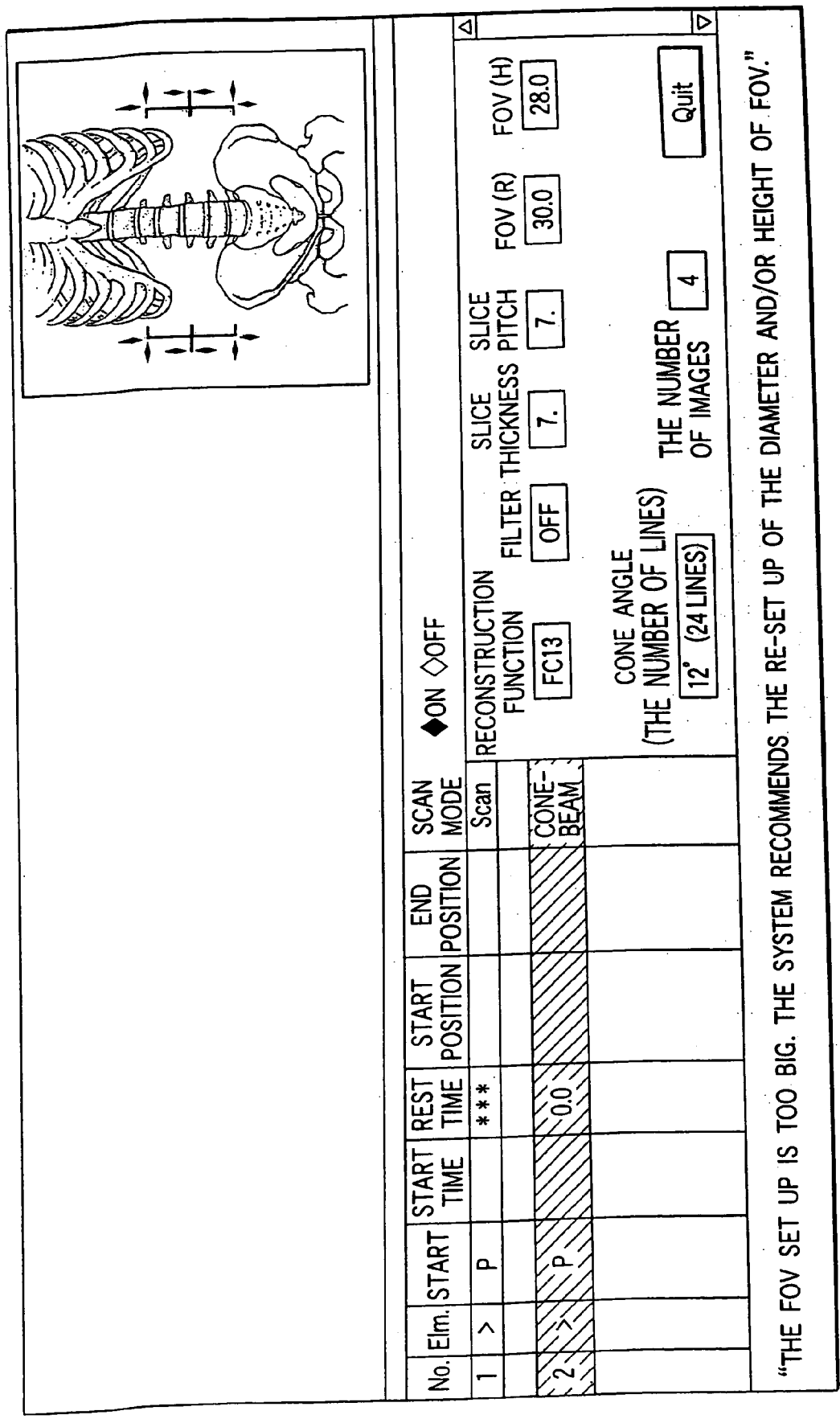
FIG. 20 is a view showing a GUI for scan condition setting which is provided by a console in FIG. 15.

A situation in which part of the reconstruction area FOV is not irradiated with X-rays due to this limiter can be easily determined by a geometrical calculation on the basis of the radius and height of the reconstruction area FOV and the maximum width of the sensitivity area of the X-ray detector 34 in the slice direction, and if it is variable, the distance between the X-ray focal point of the X-ray tube 31 and the X-ray detector 34. In addition to the above situation determination function, the gantry controller 38 or computer 39 has a function of, when the above situation is determined, displaying a message indicating the corresponding information or prompting re-setup on the collimator 32 and also has a function of calculating the volume ratio of the area irradiated with no X-rays to the set reconstruction area FOV and displaying the resultant value, as shown in FIG. 20. The operator can determine by himself on the basis of the volume ratio whether to force a scan or re-setup, and input a command corresponding to the determination.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray computed tomography apparatus comprising:
an X-ray tube configured to generate X-rays diverging in channel and slice directions;
a collimator which has an aperture that is variable in the slice direction and limits a divergence angle of the X-rays in the slice direction in accordance with the aperture;
an X-ray detector which has a plurality of X-ray detection elements for detecting X-rays transmitted through an object to be examined, the plurality of X-ray detection elements being arrayed in the channel and slice directions;
an input device configured to set a substantially cylindrical reconstruction area;
an image reconstructing unit configured to reconstruct image data within the set reconstruction area on the basis of an output from said X-ray detector;
a divergence angle determining unit configured to determine a divergence angle of the X-rays in the slice direction on the basis of a radius and height of the set reconstruction area; and
a control unit configured to control the aperture of said collimator in accordance with the determined divergence angle.

2. An apparatus according to claim 1, wherein said control unit controls the aperture of said collimator to irradiate the entire reconstruction area with the X-rays.

3. An apparatus according to claim 1, wherein said divergence angle determining unit determines the divergence angle such that the X-ray comes into contact with an edge of one end face of the reconstruction area and the X-ray comes into contact with an edge of the other end face of the reconstruction area.

4. An apparatus according to claim 1, wherein said divergence angle determining unit determines the aperture of said collimator such that a thickness of X-rays coincides with a length of the reconstruction area at a position closer to said X-ray tube than a center axis of the reconstruction area by a radius of the reconstruction area.

5. An apparatus according to claim 1, further comprising a storing unit configured to store various relationships between the radius and height of the reconstruction area and the aperture of said collimator.

6. An apparatus according to claim 1, further comprising a display configured to output a message for prompting are-setup of the radius and height of the reconstruction area when the radius and height of the reconstruction area cause a situation in which the reconstruction area cannot be entirely irradiated with the X-rays due to a limitation imposed on said X-ray detector in terms of a physical size.

7. An apparatus according to claim 1, wherein the height of the reconstruction area is associated with a slice thickness and the number of slices.

* * * * *